United States Patent [19]
Czarnecki

[11] 3,994,170
[45] Nov. 30, 1976

[54] LIQUID SAMPLER

[76] Inventor: Andrew J. Czarnecki, 100 Meadow Run, Hamburg, N.Y. 14075

[22] Filed: Sept. 11, 1975

[21] Appl. No.: 612,559

[52] U.S. Cl. ............................................. 73/421 B
[51] Int. Cl.² ............................................ G01N 1/14
[58] Field of Search .......... 73/421 R, 421 B, 422 R

[56] References Cited
UNITED STATES PATENTS

| | | | |
|---|---|---|---|
| 800,819 | 10/1905 | Platt | 73/421 B |
| 1,108,278 | 8/1914 | Thomas | 73/422 R |
| 2,164,498 | 7/1939 | Clark | 73/421 B |

*Primary Examiner*—S. Clement Swisher
*Attorney, Agent, or Firm*—Allen J. Jaffe

[57] ABSTRACT

A liquid sampler having an outer cylindrical liquid collecting container provided with a longitudinal opening or slot in the wall thereof, an inner tubular member mounted for rotation in the outer container provided with a substantial spiral slot or opening in the wall thereof whereas as the inner member rotates the longitudinal slot and the spiral slot provide a moving aperture for the collection of liquid samples at varying depths.

6 Claims, 3 Drawing Figures

LIQUID SAMPLER

The present invention relates to liquid samplers and, more particularly, to liquid samplers that automatically collect samples from moving bodies of water or from conduits at varying depths thereof.

For proper chemical analysis of bodies of water such as streams or conduits, regulatory agencies require that the sample taken be representative of the stream and proportional to its flow. Thus, it is insufficient to provide samples of, say, the bottom water only since pollutants or the like may be present at one or more depths and on the surface.

It is therefore an object of the present invention to provide a simple, and effective liquid sampler which is capable of collecting samples of liquid from the entire cross-section, including the surface waters, of conduits or streams in a single operation. It is a further object to provide a sampler which will take varying quantities of the sample stream, depending on the streams flow automatically.

Basically, the liquid sampler according to the present invention comprises; a generally cylindrical tubular container having a closed bottom end, a longitudinal opening in the wall thereof, a generally cylindrical tubular member mounted for rotation with respect to the container about the longitudinal axis thereof, a substantially spiral opening in the member extending about the periphery thereof and means imparting relative rotation between the container and the member whereby the longitudinal opening and the spiral opening coact to provide an aperture moving longitudinally of the container permitting the collection therein of liquid from varying depths of a body of liquid.

The longitudinal slot may be substantially rectangular or it may be increasingly tapered from the bottom of the container towards the top thereof to compensate for the higher pressures at greater depths of the body of liquid such that equal volumes are collected therein from all depths.

BRIEF DESCRIPTION OF THE DRAWINGS

For a fuller understanding of the present invention reference should now be had to the following detailed description thereof taken in conjunction with the accompanying drawings, wherein.

DESCRIPTION OF THE PREFERRED EMBODIMENT

Figure 1:
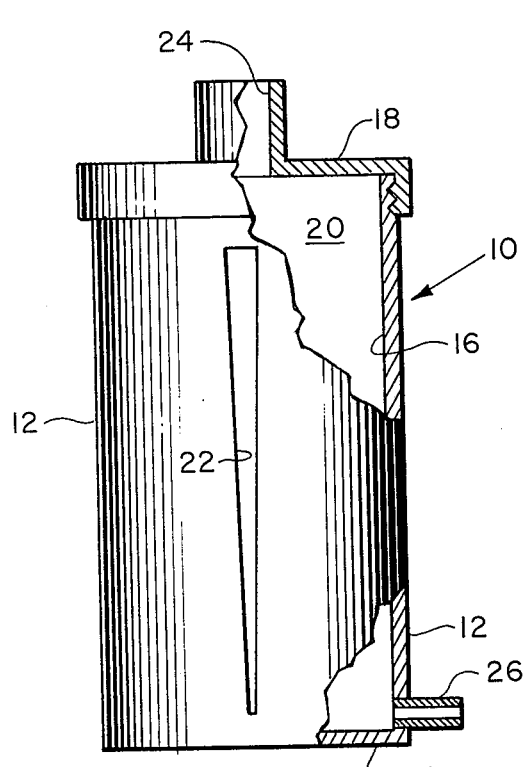
FIG. 1 is an elevational view of the liquid collection container with parts thereof broken away in section.

Referring now to the drawings and, more particularly, FIG. 1 the sampler container is generally depicted at 10 and comprises a substantially cylindrical body 12 having a closed bottom end 14, a side wall 16 and a removable cap or cover 18 defining an interior collection chamber 20.

A longitudinal slot or opening 22 extends along the length of sidewall 16 and provides communication between chamber 20 and the exterior thereof. Although slot 22 may be a suitable shape such as rectangular, the same is depicted as increasingly tapered in a direction from the bottom end 14 towards cap 18 for a purpose to become apparent hereinbelow.

Cap 18 includes as an integral part thereof an upwardly projecting hollow bushing or collar 24. A sample removal conduit or nipple 26 is suitably affixed to a lower portion of side wall 16 and passes therethrough.

Figure 2:
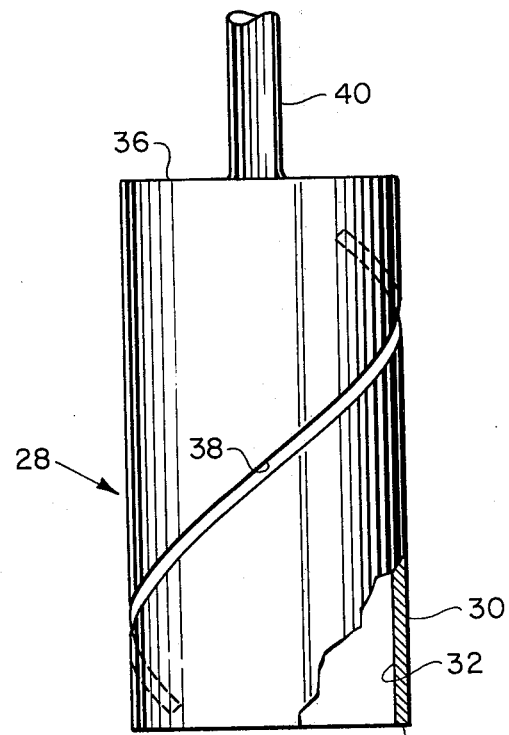
FIG. 2 is an elevational view of the tubular inner member with parts thereof broken away in section.

An inner tubular member generally depicted at 28 is located in chamber 20 of outer member 12 and is adapted to rotate with respect thereto. As illustrated in FIG. 2, member 28 comprises a generally cylindrical and hollow body 30 defining an inner peripheral wall 32 open at bottom end 34 and closed at upper end 36. A generally spiral or helical slot 38 is located in wall 32 for placing the exterior thereof in communication with the interior thereof. The circumferential extent of slot 38 is preferably less than 360 degrees for a purpose to become apparent hereinbelow.

A central shaft 40 extends upwardly from end 36, passes through collar 24 and is connected for rotation to suitable drive means such as a motor M, which may be operated by appropriate circuitry (not illustrated).

Figure 3:
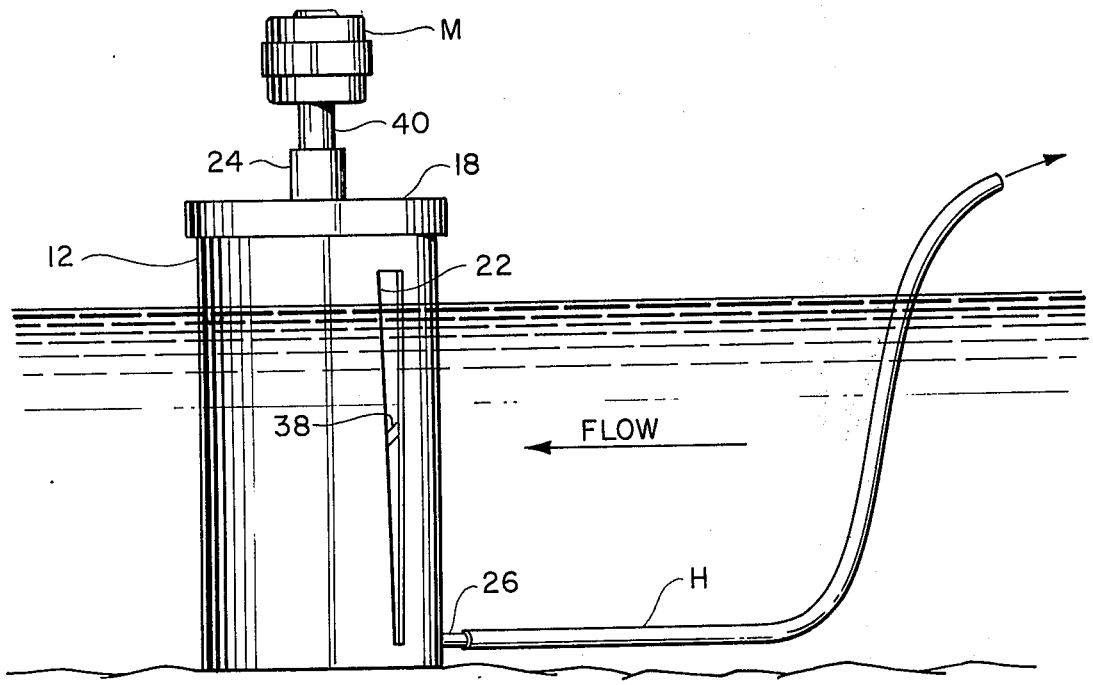
FIG. 3 is an elevational view of the liquid sampler assembly located in a body of liquid.

In the operation of the liquid sampler according to the present invention, member 28 is located in chamber 20 and the sampler is placed in a source of liquid to be sampled. Slot 22 is preferably located above the surface water such that as the flow rate of the stream increases the slot will accommodate the resultant increased depth and take samples automatically at the new surface levels. As illustrated in FIG. 3 slot 22 faces the direction of flow of the liquid to be sampled, such that as member 28 is rotated with respect to member 12 slot 38 coacts with slot 22 to define a vertically moving port means which permits the collection of liquid samples in chamber 20 from all depths traversed by such moving port means. Since the circumferential extent of spiral slot 38 is less than 360°.

There will be at least one position where liquid is blocked from entering chamber 20. In this manner the sampler can be operated, in a cyclic fashion or continuously as desired. A hose H may be connected at one end to nipple 26 and at its other end to suitable pumping means (not illustrated) for the withdrawal process.

Slot 22 is illustrated as tapered to compensate for the increasing liquid pressures at greater depths below the surface, thereby permitting collection of substantially equal volumes at each depth. If it is not desirable to collect equal volumes, slot 22 need not be tapered.

Although a preferred embodiment of the present invention has been disclosed and described, changes will obviously occur to those skilled in the art; it is therefore intended that the present invention be limited only by the scope of the appended claims.

I claim:
1. A liquid sampler, comprising;
   a. a sample container defining a collection chamber,
   b. a longitudinal tapered slot in said container,
   c. a hollow member mounted for rotation with respect to said sample container, and
   d. a spiral opening in said hollow member coacting with said longitudinal slot to provide a longitudinally moving port as said hollow member rotates with respect to said sample container whereby sample liquid is permitted to flow into said collection chamber from varying depths below the surface thereof.

2. The sampler according to claim 1, wherein;
   f. said sample container is substantially cylindrical having a closed bottom end and substantially closed top end except for a central opening therethrough, and g. said hollow member is substantially cylindrical and mounted interiorly of said container having a shaft passing through said central opening for imparting rotary motion to said hollow member.

3. The sampler according to claim 2, wherein;

h. the circumferential extent of said spiral opening is less than 360° whereby said chamber is blocked from communication with a liquid to be sampled in at least one position of said hollow member with respect to said sample container.

4. The sampler according to claim 3, wherein;

i. said longitudinal slot faces against the direction of flow of a liquid sample in which said sampler is emersed.

5. The sampler according to claim 1, wherein;

e. said sample container is substantially cylindrical having a closed bottom end and a substantially closed top end except for a central opening therethrough, f. said hollow member is substantially cylindrical and mounted interiorly of said container having a shaft passing through said central opening for imparting rotary motion to said hollow member, and g. said longitudinal opening faces against the direction of flow of a liquid sample in which said sampler is emersed.

6. The sampler according to claim 1, wherein;

e. the extent of said longitudinal opening is less than the vertical extent of said spiral opening whereby said chamber is blocked from communication with a liquid to be sampled during at least one position of said hollow member with respect to said sample container.

* * * * *